(12) United States Patent
Guo et al.

(10) Patent No.: US 9,212,345 B2
(45) Date of Patent: Dec. 15, 2015

(54) SYSTEM AND METHOD FOR PRODUCING TISSUE-ENGINEERED MATERIAL

(71) Applicant: NATIONAL CHENG KUNG UNIVERSITY, Tainan (TW)

(72) Inventors: How-Ran Guo, Tainan (TW); Chao-Lin Chen, Tainan (TW); Jin-Jia Hu, Hsinchu (TW); Yung-Chun Lee, Taipei (TW); Chung-Jen Chung, Tainan (TW)

(73) Assignee: National Cheng Kung University, Tainan (TW)

( * ) Notice: Subject to any disclaimer, the term of this patent is extended or adjusted under 35 U.S.C. 154(b) by 103 days.

(21) Appl. No.: 13/958,899

(22) Filed: Aug. 5, 2013

(65) Prior Publication Data
US 2014/0120619 A1    May 1, 2014

(30) Foreign Application Priority Data
Oct. 30, 2012   (TW) .............................. 101140127 A

(51) Int. Cl.
*C12M 1/42*   (2006.01)
*A61F 2/06*   (2013.01)

(52) U.S. Cl.
CPC ................ *C12M 35/04* (2013.01); *A61F 2/062* (2013.01)

(58) Field of Classification Search
None
See application file for complete search history.

(56) References Cited

PUBLICATIONS

Campbell et al., "Novel Vascular Graft Grown Within Recipient's Own Peritoneal Cavity" (1999) Circulation Research, vol. 85: 1173-1178.*
Niklason et al. "Functional Arteries Grown in Vitro" (1999) Science, vol. 284: 489-493.*

* cited by examiner

*Primary Examiner* — Robert Yamasaki
*Assistant Examiner* — Teresa E Knight
(74) *Attorney, Agent, or Firm* — Nixon & Vanderhye P.C.

(57) ABSTRACT

A system for producing a tissue-engineered material includes a hollow member and a mechanical stimulating unit. The hollow member is adapted to be implanted in a peritoneal cavity, and is to be positioned in the peritoneal cavity in a manner that a part of the hollow member contacts an inner wall surface of the peritoneal cavity for enabling formation of a biological tissue that encapsulates the hollow member. The mechanical stimulation unit is coupled to the hollow member and configured to provide a periodic mechanical stimulus to the biological tissue by periodically causing the hollow member to expand and contract. A method for producing the aforesaid tissue-engineered material is also disclosed.

6 Claims, 3 Drawing Sheets

SYSTEM AND METHOD FOR PRODUCING TISSUE-ENGINEERED MATERIAL

CROSS-REFERENCE TO RELATED APPLICATION

This application claims priority of Taiwanese Application No. 101140127, filed on Oct. 30, 2012.

BACKGROUND OF THE INVENTION

1. Field of the Invention

The invention relates to a system and a method for producing a tissue-engineered material, more particularly to a system and a method for producing a tissue-engineered material in a living subject.

2. Description of the Related Art

In clinical practice, many patients with atherosclerosis or chronic kidney disease may encounter situations that need replacement/transplantation of natural, artificial or tissue-engineered blood vessels. The natural origins may be autografts, decellularize-processed allografts or xenografts, and the artificial materials may be made of synthetic non-biodegradable materials including polyester, polypropylene, and expandable-PTFE, or made of biodegradable materials including polyglycolic acid (PGA) and poly-L-lactic acid (PLLA).

However, allografts and xenografts are rejected by the immune systems of the recipients, thus need thorough decellularization and other processes, resulting in increased risks of the exposure to foreign proteins and process-related chemicals. Meanwhile, the artificial materials often cause foreign body related chronic inflammation and need further treatments and processes to achieve a long-term patency.

In recent years, with the breakthroughs in the tissue-engineering field, many researchers have started investigating the methods for growing autologous cells/tissues outside the human body (in vitro) that are capable of being transplanted directly to the patients. It has been acknowledged that mechanical properties of the tissue cultured in vitro can be dramatically enhanced by applying a periodic mechanical stimulation to it. However, the in vitro cultured tissues are not always durable enough to meet the mechanical strength requirements; bioreactors that are used to grow the in vitro autologous tissues cannot completely mimic the environment in vivo, and additives (such as bovine serum) during the culture session might cause adverse consequences.

SUMMARY OF THE INVENTION

Therefore, the object of the present invention is to provide a system and a method for producing a tissue-engineered material in vivo.

According to one aspect of the present invention, a system for producing a tissue-engineered material in a peritoneal cavity of a living subject includes:

a hollow member adapted to be implanted in the peritoneal cavity, wherein the hollow member is made of a biocompatible and fluid-impermeable material that is expansible and contractible and is to be positioned in the peritoneal cavity in a manner that a part of the hollow member contacts an inner wall surface of the peritoneal cavity for enabling formation of a biological tissue that encapsulates the hollow member; and a mechanical stimulation unit coupled to the hollow member and configured to provide, during a stimulation session, a periodic mechanical stimulus to the biological tissue being formed on the hollow member by periodically introducing a fluid to flow into and out of the hollow member to cause the hollow member to expand and contract accordingly.

According to another aspect of the present invention, a method for producing a tissue-engineered material in a peritoneal cavity of a living subject includes the following steps of:

(a) implanting a hollow member in the peritoneal cavity, wherein the hollow member is made of a biocompatible and fluid-impermeable material that is expansible and contractible and is positioned in the peritoneal cavity in a manner that a part of the hollow member contacts an inner wall surface of the peritoneal cavity for enabling formation of a biological tissue that encapsulates the hollow member; and (b) during a stimulation session, providing a periodic mechanical stimulus to the biological tissue being formed on the hollow member by periodically introducing a fluid to flow into and out of the hollow member to cause the hollow member to expand and contract accordingly.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
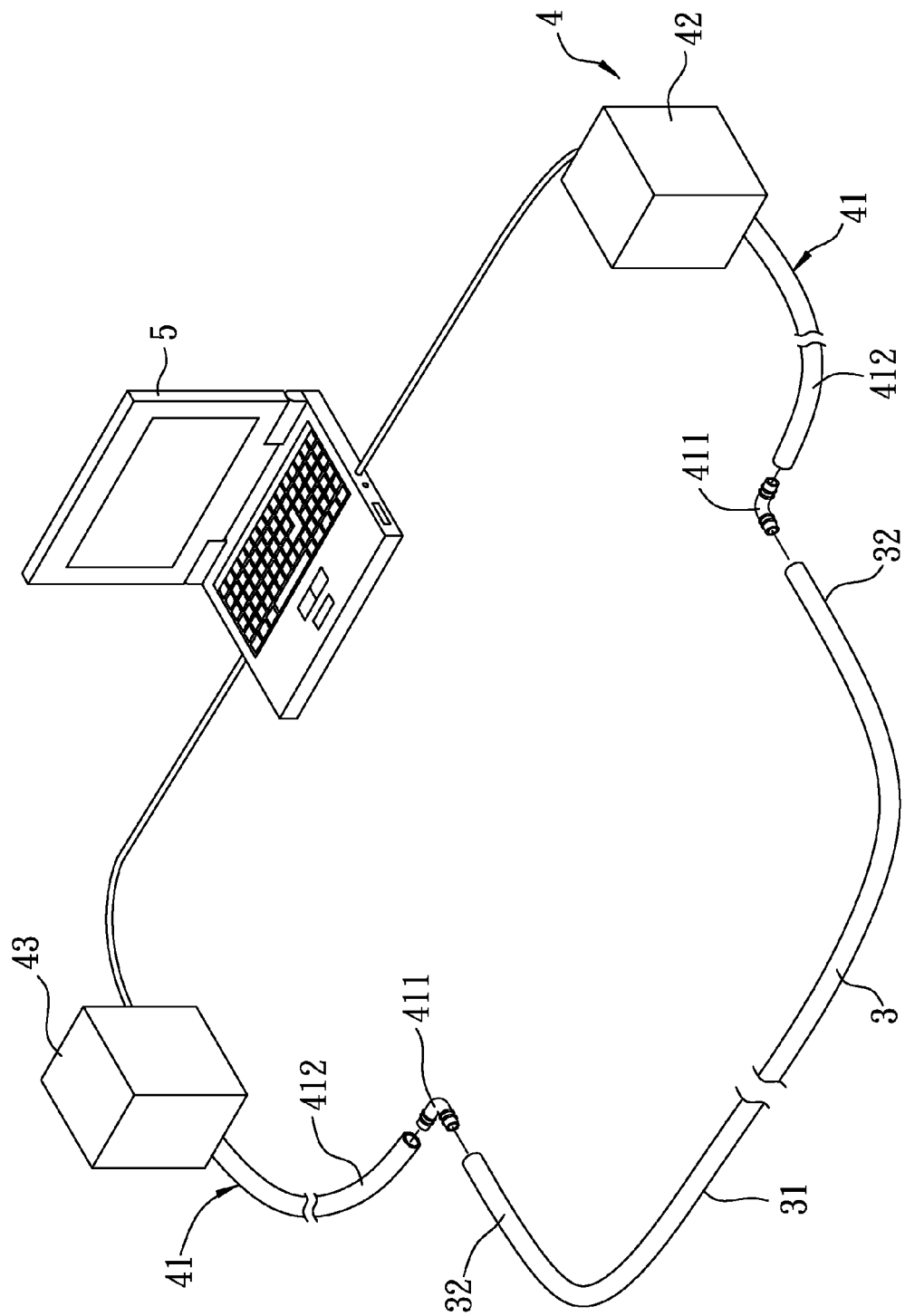
FIG. 1 is a schematic diagram of a preferred embodiment of a system for producing a tissue-engineered material in a peritoneal cavity according to the invention.
Figure 2:
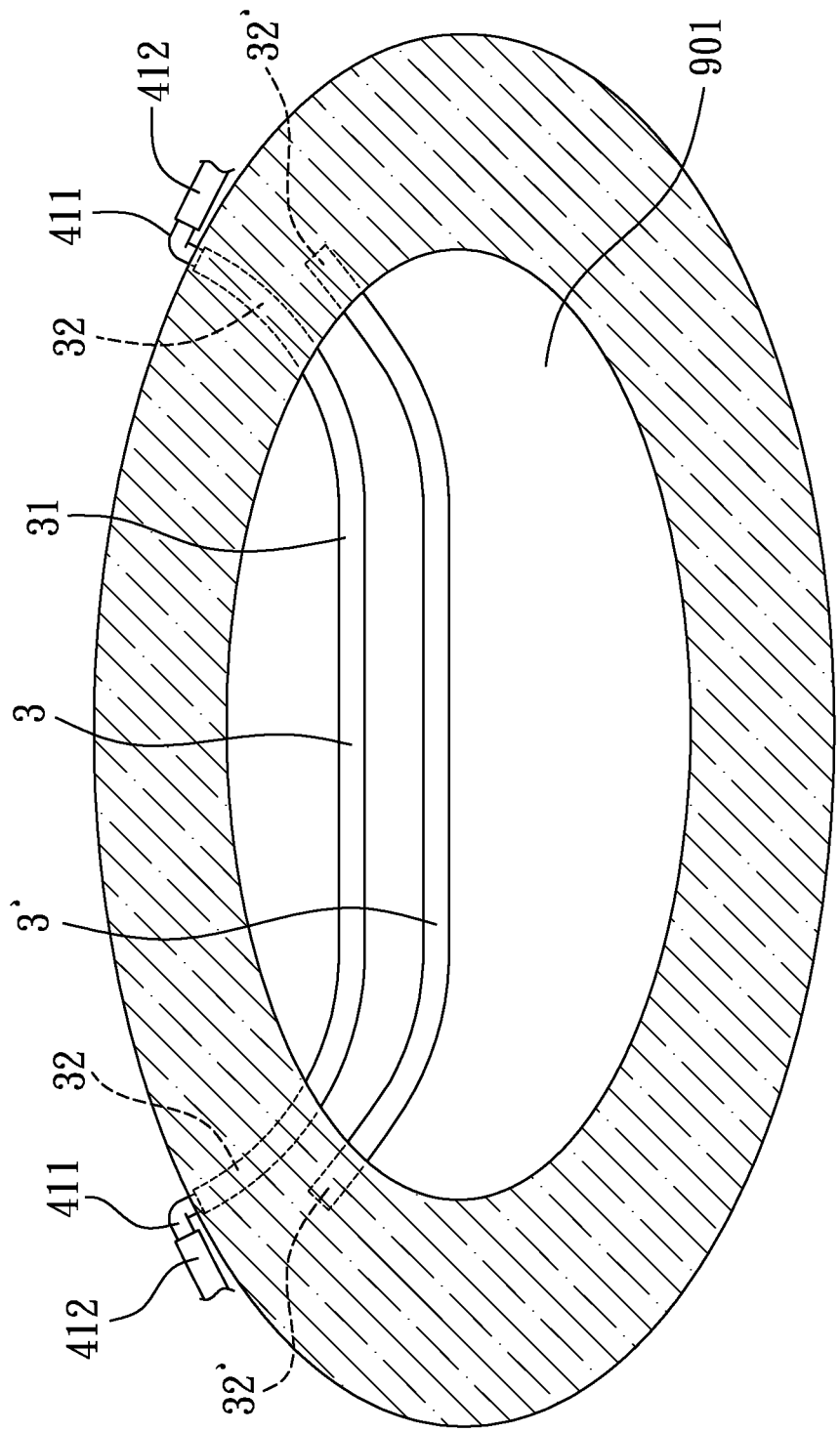
FIG. 2 is a schematic diagram illustrating that a hollow member of the preferred embodiment is implanted in a peritoneal cavity.

Referring to FIGS. 1 and 2, the preferred embodiment of a system for producing a tissue-engineered material in a peritoneal cavity 901 of a living subject includes a hollow member 3, a mechanical stimulation unit 4, and a control unit 5.

The hollow member 3 is made of a biocompatible and fluid-impermeable material and has an elastic segment 31 that has opposite ends, that is elastically deformable (e.g., expansible and contractible), and that is to be disposed in the peritoneal cavity 901, and a pair of securing subcutaneous segments 32 that extend from and are in fluid communication with the opposite ends of the elastic segment 31 respectively, that are to be extended outwardly of the peritoneal cavity 901, and that are adapted to position the elastic segment 31 in the peritoneal cavity 901 in a manner that a part of the elastic segment 31 contacts an inner wall surface of the peritoneal cavity 901 for enabling formation of a biological tissue that encapsulates the elastic segment 31.

In this embodiment, the hollow member 3 is configured in a tubular shape. However, the size and the shape of the hollow member 3 are dependent on the size and shape requirements of the tissue-engineered material and are not limited hereto. For example, the elastic segment 31 of the hollow member 3 may be configured in a sac shape. Moreover, the hollow member 3 could include a plurality of elastic segments 31 with the same or different sizes.

The mechanical stimulation unit 4 includes a pair of delivery pipe units 41 each of which is coupled to and in fluid communication with a respective one of the securing segments 32, a pressurizing device 42 that is coupled to and in fluid communication with one of the delivery pipe units 41 and that is operable to introduce a fluid that flows into and out of the hollow member 3, and a pressure sensing device 43 that is connected to the other one of the delivery pipe units 41 and that is operable for detecting the pressure of the fluid in the hollow member 3 and for generating an output signal corresponding to the pressure. Each of the delivery pipe units 41 includes a duct member 411 that is connected to and in fluid communication with the respective one of the securing segments 32, and a pipe member 412 connected to and in fluid communication with the duct member 411 and connected to a corresponding one of the pressurizing device 42 and the pressure sensing device 43. In this embodiment, the pressurizing device 42 is a syringe pump (V3 syringe pump, commercially available from Kloehn, USA), but it is not limited hereto.

The control unit 5 is electrically coupled to the pressurizing device 42 and the pressure sensing device 43, and is operable for receiving the output signal from the pressure sensing device 43 and for controlling operation of the pressurizing device 42 according to the output signal to control e.g., duration of the stimulation session, frequency of introducing the fluid, and the pressure of the fluid being introduced into the hollow member 3. Preferably, the control unit 5 is a programmable device.

Figure 3:
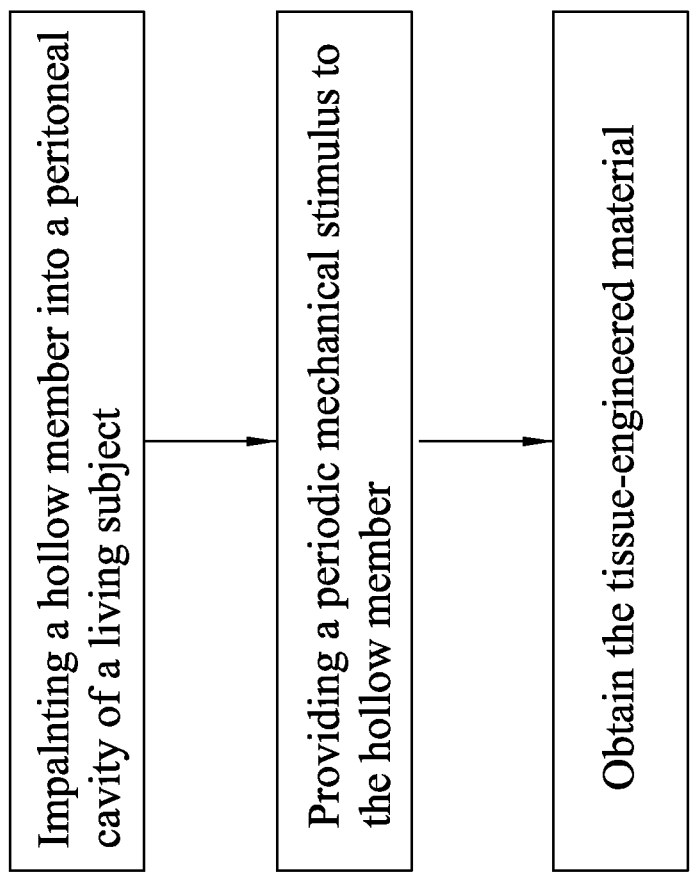
FIG. 3 is a flowchart of the preferred embodiment of a method for producing a tissue-engineered material in a peritoneal cavity according to the present invention.

Referring to FIG. 3 as well as FIGS. 1 and 2, the preferred embodiment of a method according to the present invention includes the following steps of:

(a) implanting the hollow member 3 in the peritoneal cavity 901, wherein the hollow member 3 is positioned in the peritoneal cavity 901 in a manner that a part of the hollow member 3 contacts an inner wall surface of the peritoneal cavity 901 for enabling formation of a biological tissue that encapsulates the hollow member 3; and (b) during a stimulation session, providing from the mechanical stimulation unit 4 a periodic mechanical stimulus to the biological tissue being formed on the hollow member 3 by periodically introducing a fluid to flow into and out of the hollow member 3 to cause the hollow member 3 to expand and contract accordingly.

Preferably, the method further includes a step:

(c) removing the hollow member 3 from the peritoneal cavity 901 and harvesting the biological tissue from the hollow member 3 to obtain the tissue-engineered material.

To be specific, in step (a), the elastic segment 31 of the hollow member 3 is disposed in the peritoneal cavity 901, and the pair of securing segments 32 extend outwardly of the peritoneal cavity 901 and are embedded in a subcutaneous space so as to position the elastic segment 31 in the peritoneal cavity 901.

Preferably, in step (b), the fluid is periodically introduced into and drawn out of the hollow member 3 from one of the securing segments 32 during the stimulation session.

In step (b), duration of the stimulation session, frequency of introducing the fluid, and pressure of the fluid being introduced into the hollow member 3 are adjusted by the control unit 5 through controlling operation of the pressurizing device 42 according to the output signal from the pressure sensing device 43.

Preferably, step (b) is repeated to conduct multiple stimulation sessions within a predetermined time period.

In this embodiment, the fluid is a liquid. However, the fluid may be gas while implementing other embodiments according to the present invention. Also, the duration of the stimulation session, frequency of introducing the fluid, and pressure of the fluid being introduced into the hollow member 3 are dependent upon the size, the shape, and the material of the hollow member 3, and are not limited hereto.

EXAMPLES

Example 1

For producing the tissue-engineered material of Example 1 according to the preferred embodiment of the present invention, a silicone tube (i.e., a hollow member 3) was implanted into a peritoneal cavity 901 of a Sprague-Dawley (SD) rat. The silicone tube has an inner diameter of 1 mm, an outer diameter of 3 mm, and a length of 6 cm inside peritoneal cavity, and 27 SD rats were subjected to the implantation. While implanting the silicone tube, a small incision was made in each of left and right sides of an abdominal wall of the SD rat. The silicone tube was inserted into the peritoneal cavity 901 from one of the incisions and had an elastic segment 31 retained in the peritoneal cavity 901. The elastic segment 31 of the silicone tube had a part that contacts an inner surface of the peritoneum for enabling the formation of a biological tissue that encapsulates the silicone tube. The silicone tube had a pair of securing segments 32 and each of the securing segments 32 was extended outwardly from the elastic segment 31 and penetrated the abdominal wall to be sutured and embedded in subcutaneous tissues of the back of the SD rat for securing the silicone tube. Then, each of the securing segments 32 was coupled to and in fluid communication with a duct member 411 of a delivery pipe unit 41, wherein each of the duct member 411 was partially inserted into the SD rat body with one end located outside of the SD rat body for coupling with a pipe member 412 of a corresponding one of the delivery pipe units 41. The two incisions were closed with sutures after the implantation and 7 days of a recovery period was given to the SD rat before mechanical stimulation performed.

It is worth noting that the design of the silicone tube to have the securing segments 32 secured and embedded subcutaneously in the SD rat not only positions the elastic segment 31 in the peritoneal cavity 901, but also prevents the germs invading the peritoneal cavity 901 from the body surface of the SD rat via the silicone tube, so as to lower the risk of causing the infection of the peritoneal cavity 901.

After the resting period, each of the 27 SD rats was subjected to a periodic stimulation session. During the periodic stimulation session, the pipe member 412 of each of the delivery pipe units 41 was coupled to and in fluid communication with the respective duct member 411. A syringe pump (i.e., the pressurizing device 42) was then coupled to one of the pipe members 412 for introducing water to flow into and out of the respective pipe member 412, and a pressure sensing device 43 was coupled to the other one of the pipe members 412 for detecting the water pressure flowing in the silicone tube and the delivery pipe units 41. The water was periodically introduced into and drawn out of the silicone tube from one of the securing segments 32 by the syringe pump so as to cause the silicone tube to expand and contract accordingly and to generate pulsations thereof. The frequency of introducing the water into and out of the silicone tube was about 0.3 Hz (3 to 4 seconds for a pumping cycle), and the maximum water pressure being introduced into the silicone tube during the pumping cycle was 4 $Kg/cm^2$. The relationship between the water pressure and an (diameter) inflation rate of the silicone tube based on the material property of the silicone tube may be illustrated by the following: 4.1 $Kg/cm^2$=12%, 3.5 $Kg/cm^2$=10.3%, and 3 $Kg/cm^2$=6.6%. The stimulation session lasted for 8 hours per day, and was repeated for 15 consecutive days. After 8 hours of the stimulation session, the two pipe members 412 were disconnected from the respective duct members 411 to allow the SD rats to rest. After the 15 days of repeating stimulation sessions, the silicone tube was removed from each of the SD rats and the biological tissue which encapsulates the elastic segment 31 and the securing segments 32 was harvested, and the tissue-engineered material of Example 1 was obtained.

It should be noted that the tissue-engineered material encapsulated both of the elastic segment 31 in the peritoneal cavity 901 and the securing segments 32 subcutaneously. Therefore, the tissue-engineered material of Example 1 was divided into a tubular sample 1(a), which was formed on the elastic segment 31, and a tubular sample 1(b) which was formed on the securing segments 32. Both of the samples 1(a) and 1(b) were subjected to the following analysis.

Comparative Example 1

The method for producing the tissue-engineered material of Comparative Example 1 is similar to that of Example 1. The difference between the Example 1 and Comparative Example 1 resides in that no mechanical stimulus was provided to the biological tissue being formed on the silicone tube of Comparative Example 1. That is, the silicone tube of Comparative Example 1 was not connected to the delivery pipe units 41 but merely had the elastic segment 31' thereof being positioned in the peritoneal cavity 901 and the two securing segments 32' being sutured and embedded subcutaneously in the same SD rat as Example 1. Here, the silicone tube for growing the tissue-engineered material of Comparative Example 1 was implanted into the peritoneal cavity 901 together with that of Example 1 but spaced apart from each other in order to form the biological tissues separately. After the 15 days during which no mechanical stimulation was provided, the silicone tube of Comparative Example 1 was removed from the peritoneal cavity 901 together with that of Example 1, and the biological tissue of Comparative Example 1 was harvested from the respective silicone tube to obtain the tissue-engineered material of Comparative Example 1. Likewise, the tissue-engineered material of Comparative Example 1 was divided into a tubular sample 2(a), which was formed on the elastic segment 31', and a tubular sample 2(b) which was formed on the securing segments 32'. Both of the samples 2(a) and 2(b) were subjected to the following analysis.

[Mechanical Property Analysis]

1. Compliance Testing

The tissue-engineered material of each of the tubular samples 1(a), 1(b), 2(a), and 2(b) was immersed in a saline solution with two ends connected to and in fluid communication with a mechanical testing platform for providing a tensile stress thereto with an elongation rate of about 10%. During a testing cycle, a fluid was introduced by the mechanical testing platform to flow into and out of each of the samples with a fluid injection (or drawing) rate of 0.2 ml/min. The fluid pressure during the testing cycle ranged from 10 mmHg to 140 mmHg, and the total number of the testing cycle was 14. The compliance of each of the samples was calculated by applying the following formula (I):

$$\text{Compliance}(\%/100 \text{ mmHg}) = \frac{(D_{140} - D_{70})/D_{70}}{70 \text{ mmHg}} \times 10^4 \quad (I)$$

wherein $D_{140}$ represents the outer diameter of the tissue-engineered material while the fluid pressure in the samples is 140 mmHg, $D_{70}$ representing the outer diameter of the tissue-engineered material while the fluid pressure in the samples is 70 mmHg. The compliance result of each of the samples is listed in Table 1.

2. Burst Pressure Testing

After the compliance test, the tissue-engineered material of each of the samples was subjected to a burst pressure testing by continuously introducing the fluid into the tissue-engineered material with a feeding rate of 0.2 ml/min until the tissue-engineered material burst out and the burst pressure of the tissue-engineered material of each of the samples was recorded and listed in Table 1.

3. Suture Retention Force Testing

The tissue-engineered material of each of the samples was subjected to a suture retention force testing. A 6-0 Prolene suture was placed to connect the sample to a step motor-operated extending device. The suture needle was placed into each of the sample edge with a 2 mm bite at one end while the other end of each of the samples was secured, followed by driving the step motor to increase the tension force of the suture until the breakage of the sample edge. The result of the maximum suture retention force of each of the samples is listed in Table 1.

[Tissue Slicing and Colorimetric Analysis]

The tissue-engineered material of each of the samples was fixed by 10% buffered formaldehyde overnight and followed by being embedded in paraffin. Each of the samples was sectioned at 4 μm thickness and was subjected to hematoxylin-eosin stain and Masson trichrome stain. For each of the samples, 4 color images were acquired with a photomicroscope and a digital camera, and the content of collagen of each of the examples was determined by image analysis. The result of each of the samples is listed in Table 1.

TABLE 1

| | Sample 1(a) | Sample 1(b) | Sample 2(a) | Sample 2(b) |
|---|---|---|---|---|
| Burst Pressure(psi) mean ± SD | 28.08 ± 22.07 | 24.41 ± 17.34 | 9.39 ± 6.86 | 17.93 ± 11.04 |
| Suture Retention Force(gw) mean ± SD | 81.86 ± 49.65 | 82.19 ± 46.77 | 35.3 ± 18.28 | 64.75 ± 21.09 |
| Collagen Content Ratio mean ± SD | 0.4744 ± 0.1911 | 0.4375 ± 0.0944 | 0.3269 ± 0.0370 | 0.3369 ± 0.1210 |
| Compliance (% per 100 mmHg) mean ± SD | 1.69 ± 0.83 | 1.57 ± 0.70 | 2.28 ± 0.59 | 1.34 ± 0.36 |
| Wall Thickness (mm) mean ± SD | 0.2349 ± 0.1546 | 0.1739 ± 0.1082 | 0.1568 ± 0.1354 | 0.0957 ± 0.0826 |

[Results]

As shown in Table 1, the burst pressure of Sample 1(a) is 28.08±22.07 psi, which is obviously larger than that of Sample 2(a) (9.39±6.86 psi). The suture retention force of Sample 1(a) is 81.86±49.65 g, which is also larger than that of Sample 2(a). In the compliance test, Sample 2(a) has greater compliance result of 2.28±0.59% per 100 mmHg than that of Sample 1(a) (1.69±0.83% per 100 mmHg). As for the tubular wall thickness, Sample 1(a) (0.2349±0.1546 mm) is thicker than Sample 2(a) (0.1568±0.1354 mm). As for the content ratio of the collagen, Sample 1(a) is higher than Sample 2(a). In general, Sample 1(a) has relatively high mechanical property than that of Sample 2(a), as well as the content of the collagen in the tubular samples.

As for the Samples 1(b) and 2(b), the burst pressure of Sample 1(b) is 24.41±17.34 psi, which is obviously larger than that of Sample 2(b) (17.93±11.04 psi). The suture retention force of Sample 1(b) is 82.19±46.77 g, which is also larger than that of Sample 2(b) (64.75±21.09 g). In the compliance test, Sample 1(b) has better compliance result of 1.57±0.70% per 100 mmHg than that of Sample 2(b) (1.34±0.36% per 100 mmHg). As for the tubular wall thickness, Sample 1(b) (0.1739±0.1082 mm) is thicker than Sample 2(b) (0.0957±0.0826 mm). As for the content of the collagen, Sample 1(b) is higher than Sample 2(b).

It is worth noting that the standard deviation of the tubular wall thickness of Samples 2(a) and 2(b) are close to the corresponding mean values of the tubular wall thickness, illustrating that the varied tubular wall thickness occurs in the samples without the applied mechanical stimulation.

To sum up, by using the hollow member 3 to implant in the peritoneal cavity 901 of the living subject and to provide a mechanical stimulus to the hollow member 3, the tissue-engineered material of the present invention is capable of being formed on the hollow member 3 and having high mechanical strength. Further, since the tissue-engineered material is formed in the living subject, it is capable of being transplanted as an autograft or other autologous transplantation which dramatically lowers the inflammation and the rejection rate.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for producing a tissue-engineered material in a peritoneal cavity of a living subject, said method comprising the following steps of:
    (a) implanting a hollow member in the peritoneal cavity, wherein the hollow member is made of a biocompatible and fluid-impermeable material that is expansible and contractible and is positioned in the peritoneal cavity in a manner that a part of the hollow member contacts an inner wall surface of the peritoneal cavity for enabling formation of a biological tissue that encapsulates the hollow member; and
    (b) during a stimulation session, providing a periodic mechanical stimulus to the biological tissue being formed on the hollow member by periodically introducing a fluid to flow into and out of the hollow member to cause the hollow member to expand and contract accordingly;
    wherein, in step (a), the hollow member has an elastic segment that has opposite ends, that is elastically deformable, and that is disposed in the peritoneal cavity, and a pair of securing subcutaneous segments that extend from and are in fluid communication with the opposite ends of the elastic segment respectively, that extend outwardly of the peritoneal cavity, and that position the elastic segment in the peritoneal cavity.

2. The method as claimed in claim 1, further comprising the step of:
    (c) removing the hollow member from the peritoneal cavity and harvesting the biological tissue from the hollow member to obtain the tissue-engineered material.

3. The method as claimed in claim 1, wherein step (b) is repeated to conduct multiple stimulation sessions within a predetermined time period.

4. The method as claimed in claim 1, wherein, in step (a), the securing segments are embedded in a subcutaneous space.

5. The method as claimed in claim 1, wherein, in step (b), the fluid is periodically introduced into and drawn out of the hollow member from one of the securing segments during the stimulation session.

6. The method as claimed in claim 1, wherein step (b) includes controlling duration of the stimulation session, frequency of introducing the fluid, and pressure of the fluid being introduced into the hollow member.

* * * * *